US010247654B2

(12) United States Patent
Yu et al.

(10) Patent No.: US 10,247,654 B2
(45) Date of Patent: Apr. 2, 2019

(54) METHOD AND DEVICE FOR CALCULATING CONSUMED LIFESPAN (71) Applicants: Xiaomi Inc., Beijing (CN); Beijing Smartmi Technology Co., Ltd., Beijing OT (CN)

(72) Inventors: Jiuping Yu, Beijing (CN); Dongxu Liu, Beijing (CN); Nuo Yang, Beijing (CN)

(73) Assignee: XIAOMI INC., Haidian District, Beijing (CN)

( * ) Notice: Subject to any disclaimer, the term of this patent is extended or adjusted under 35 U.S.C. 154(b) by 176 days.

(21) Appl. No.: 15/361,499

(22) Filed: Nov. 28, 2016

(65) Prior Publication Data

US 2017/0153173 A1 Jun. 1, 2017

(30) Foreign Application Priority Data

Nov. 27, 2015 (CN) .......................... 2015 1 0846555

(51) Int. Cl.
*G01N 15/08* (2006.01)
*B01D 46/00* (2006.01)
(Continued)

(52) U.S. Cl.
CPC ......... *G01N 15/08* (2013.01); *B01D 46/0086* (2013.01); *F24F 11/30* (2018.01); *F24F 11/39* (2018.01); *G01N 2015/084* (2013.01)

(58) Field of Classification Search
CPC .. G01N 15/08; G01N 2015/084; B01D 46/00; B01D 46/0086; F24F 11/30; F24F 11/39
See application file for complete search history.

(56) References Cited

U.S. PATENT DOCUMENTS 4,341,985 A * 7/1982 Houskamp .............. B60L 11/18
                                                  180/179
5,142,238 A * 8/1992 White ..................... H03F 3/005
                                                   330/51
(Continued)

FOREIGN PATENT DOCUMENTS

CN      1894641 A      1/2007
CN      1994522 A      7/2007
(Continued)

OTHER PUBLICATIONS

Extended European Search Report for European application No. 16194474.9, dated Jun. 7, 2017.
(Continued)

*Primary Examiner* — Nguyen Q. Ha
(74) *Attorney, Agent, or Firm* — Jun He Law Offices P.C.; James J. Zhu (57) ABSTRACT A method and a device for calculating a consumed lifespan are provided. The method includes: controlling an electric motor of a purifier to rotate at a predetermined speed; acquiring a value of a sampled parameter of the electric motor, the sampled parameter being at least one of a sampled current and a sampled voltage of the electric motor; and determining a consumed lifespan of the purifier according to the acquired value of the sampled parameter, wherein the consumed lifespan is in positive correlation with the acquired value of the sampled parameter.

16 Claims, 4 Drawing Sheets (51) Int. Cl.
*F24F 11/39* (2018.01)
*F24F 11/30* (2018.01)

(56) References Cited

U.S. PATENT DOCUMENTS

| | | | |
|---|---|---|---|
| 6,334,959 B1 | 1/2002 | Sutton et al. | |
| 6,582,295 B1* | 6/2003 | Abouchaar | B01D 46/0039 340/607 |
| 2003/0070544 A1* | 4/2003 | Mulvaney | B01D 46/0086 95/25 |
| 2005/0188842 A1 | 9/2005 | Hsieh | |
| 2007/0146148 A1* | 6/2007 | Kawasaki | B01D 46/0086 340/607 |
| 2015/0330861 A1* | 11/2015 | Alsaleem | G01M 3/025 702/183 |
| 2016/0290668 A1* | 10/2016 | Taylor | F24F 11/006 |

FOREIGN PATENT DOCUMENTS

| | | |
|---|---|---|
| CN | 101876669 A | 11/2010 |
| CN | 102215914 A | 10/2011 |
| CN | 202507897 U | 10/2012 |
| CN | 102938023 A | 2/2013 |
| CN | 104165903 A | 11/2014 |
| CN | 104482602 A | 4/2015 |
| CN | 104841214 A | 8/2015 |
| CN | 104949293 A | 9/2015 |
| CN | 104990202 A | 10/2015 |
| CN | 105487459 A | 4/2016 |
| EP | 1800919 A2 | 6/2007 |
| EP | 1800919 B1 | 8/2009 |
| JP | 61259043 A * | 11/1986 |
| JP | S63156967 A | 6/1988 |
| JP | H0576713 A | 3/1993 |
| JP | H08103618 A | 4/1996 |
| JP | 2000179910 A | 6/2000 |
| JP | 2000246000 A | 9/2000 |
| JP | 2001518187 A | 10/2001 |
| KR | 20040091821 A | 11/2004 |
| KR | 20130074486 A | 7/2013 |
| RU | 2244158 C1 | 1/2005 |
| RU | 2006119726 A | 12/2007 |

OTHER PUBLICATIONS

International Search Report for International application No. PCT/CN2016/084956, dated Jul. 19, 2016.
International Search Report for PCT/CN2016/084956.
The Office Action on Japanese application No. 2016550209, dated Aug. 14, 2018.

* cited by examiner

METHOD AND DEVICE FOR CALCULATING CONSUMED LIFESPAN

CROSS-REFERENCE TO RELATED APPLICATIONS

The present application is based upon and claims priority to Chinese Patent Application No. CN201510846555.2 filed Nov. 27, 2015, the entire contents of which are incorporated herein by reference.

TECHNICAL FIELD

The present disclosure generally relates to the field of purifiers, and more particularly, to a method and a device for calculating a consumed lifespan.

BACKGROUND

A filter core in a purifier has a limited service life. The filter core has to be replaced in time when the filter core is stuck with dirt, to ensure the air purifying effect.

In a related art, when the purifier is operated at various levels of power, in order to calculate a current consumed lifespan, a service time period at each level of power is recorded, the recorded service time periods are respectively multiplied with corresponding coefficients, and the products are sum up as the current consumed lifespan.

SUMMARY

According to a first aspect of embodiments of the present disclosure, there is provided a method for calculating a consumed lifespan. The method includes the following steps: controlling an electric motor of a purifier to rotate at a predetermined speed; acquiring a value of a sampled parameter of the electric motor, the sampled parameter being at least one of a sampled current and a sampled voltage of the electric motor; and determining a consumed lifespan of the purifier according to the acquired value of the sampled parameter, wherein the consumed lifespan is in positive correlation with the acquired value of the sampled parameter.

According to a second aspect of embodiments of the present disclosure, there is provided a device for calculating a consumed lifespan. The device includes: a processor; and a memory for storing instructions executable by the processor. Wherein the processor is configured to perform: controlling an electric motor of a purifier to rotate at a predetermined speed; acquiring a value of a sampled parameter of the electric motor, the sampled parameter being at least one of a sampled current and a sampled voltage of the electric motor; and determining a consumed lifespan of the purifier according to the acquired value of the sampled parameter, wherein the consumed lifespan is in positive correlation with the acquired value of the sampled parameter.

According to a third aspect of embodiments of the present disclosure, there is provided a non-transitory computer-readable storage medium having stored therein instructions that, when executed by a processor of a purifier, causes the purifier to perform a method for calculating a consumed lifespan. The method includes the following steps: controlling an electric motor of a purifier to rotate at a predetermined speed; acquiring a value of a sampled parameter of the electric motor, the sampled parameter being at least one of a sampled current and a sampled voltage of the electric motor; and determining a consumed lifespan of the purifier according to the acquired value of the sampled parameter, wherein the consumed lifespan is in positive correlation with the acquired value of the sampled parameter.

It is to be understood that both the foregoing general description and the following detailed description are exemplary only and are not restrictive of the present disclosure.

BRIEF DESCRIPTION OF THE DRAWINGS

The accompanying drawings, which are incorporated in and constitute a part of this specification, illustrate embodiments consistent with the present disclosure and, together with the description, serve to explain the principles of the present disclosure.

DETAILED DESCRIPTION

Reference will now be made in detail to exemplary embodiments, examples of which are illustrated in the accompanying drawings. The following description refers to the accompanying drawings in which the same numbers in different drawings represent the same or similar elements unless otherwise represented. The implementations set forth in the following description of exemplary embodiments do not represent all implementations consistent with the present disclosure. Instead, they are merely examples of devices and methods consistent with aspects related to the present disclosure as recited in the appended claims.

Figure 1:
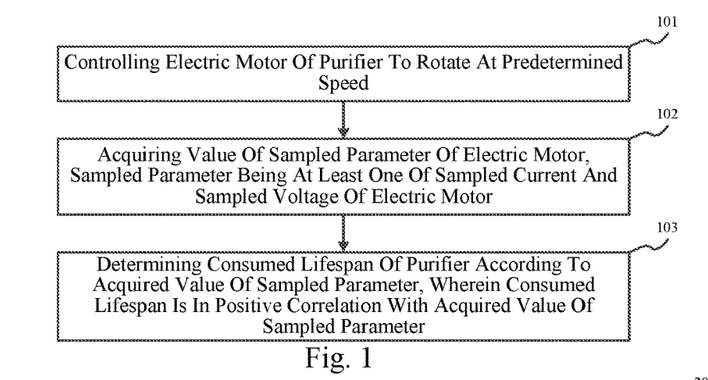
FIG. 1 is a flow chart illustrating a method for calculating a consumed lifespan according to an exemplary embodiment.

FIG. 1 is a flow chart illustrating a method for calculating a consumed lifespan according to an exemplary embodiment. The example method can be applied, for example, in a purifier. As shown in FIG. 1, the method for calculating a consumed lifespan includes the following steps.

In step 101, an electric motor of a purifier is controlled to rotate at a predetermined speed.

In step 102, a value of a sampled parameter of the electric motor is acquired, the sampled parameter being at least one of a sampled current and a sampled voltage of the electric motor.

In step 103, a consumed lifespan of the purifier is determined according to the acquired value of the sampled parameter, wherein the consumed lifespan is in positive correlation with the acquired value of the sampled parameter.

In the method for calculating a consumed lifespan provided by the present disclosure, an electric motor of a purifier is controlled to rotate at a predetermined speed; a value of a sampled parameter of the electric motor is acquired, the sampled parameter being at least one of a sampled current and a sampled voltage of the electric motor; and a consumed lifespan of the purifier is determined according to the acquired value of the sampled parameter, wherein the consumed lifespan is in positive correlation with the acquired value of the sampled parameter. Thus, based on the fact that the dirty degree of the filter core is in positive correlation with the value of the driving current of the electric motor, the dirty degree of the filter core can be determined according to the value of the sampled parameter of the electric motor, and in turn, the consumed lifespan of the filter core can be determined. In this way, it may avoid inaccuracies of determining the consumed lifespans according to the service time periods, and can improve the accuracy of calculating consumed lifespans.

Figure 2A:
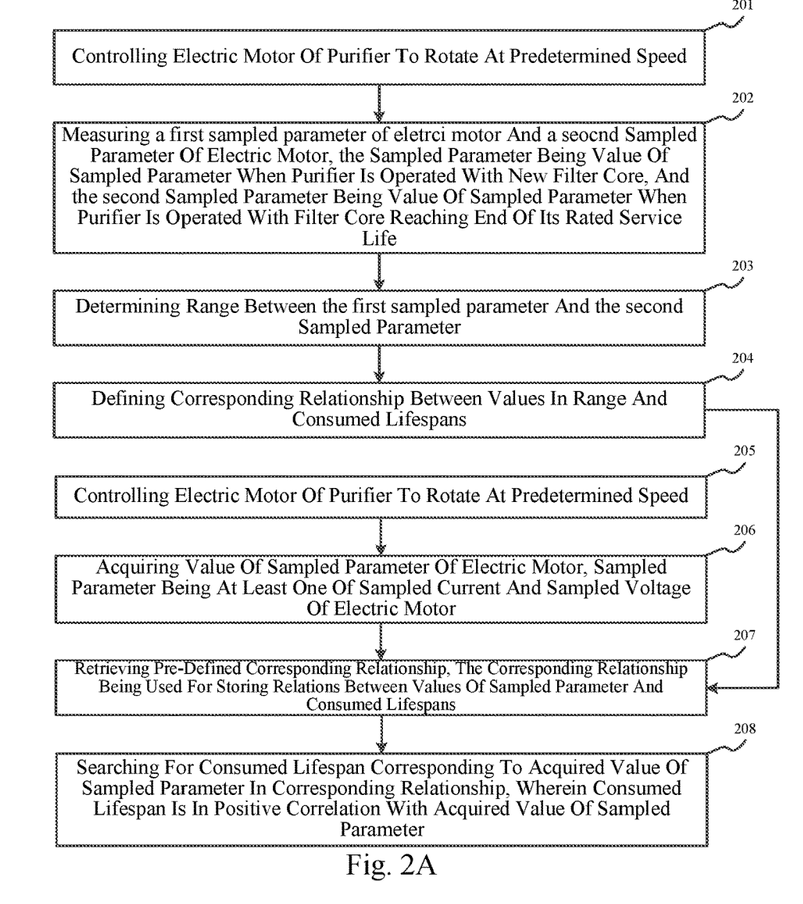
FIG. 2A is a flow chart illustrating a method for calculating a consumed lifespan according to another exemplary embodiment.

FIG. 2A is a flow chart illustrating a method for calculating a consumed lifespan according to another exemplary embodiment. This example method can be applied, for example, applied in a purifier. As shown in FIG. 2A, the method for calculating a consumed lifespan includes the following steps.

In step 201, an electric motor of a purifier is controlled to rotate at a predetermined speed.

The purifier can be controlled to purify the air by driving the electric motor of the purifier at different speeds. The higher the speed of the electric motor, the greater the driving current of the electric motor is.

In this embodiment, a user can manually adjust the speed of the electric motor to any value, and the purifier determines the value as the predetermined speed.

In step 202, a first sampled parameter of the electric motor and a second sampled parameter of the electric motor are measured. The first sampled parameter is a value of the sampled parameter when the purifier is operated with a new filter core, and the second sampled parameter is a value of the sampled parameter when the purifier is operated with the filter core reaching an end of its rated service life.

When the purifier is operated with a new filter core, the air path of the filter core is smooth. Then, the driving current of the electric motor can be small. After the filter core has been put into operation for a while, the filter core can be stuck with dirt since impurities in the air to be purified can be trapped in the filter core, such that the air path of the filter core can be less smooth than before. At this time, the driving current of the electric motor can be greater. In this regard, the dirty degree of the filter core is in positive correlation with the value of the driving current. That is, the longer the consumed lifespan is, the more dirty the filter core is, and the greater the driving current is. Base on this fact, a corresponding relationship between consumed lifespans of the purifier and values of the driving currents can be defined in advance.

Since a voltage is a product of a current value multiplying with a resistance, the consumed lifespan of the purifier can be determined according to the voltage of the electric motor. Here, the voltage is a sampled voltage of the electric motor, rather than a rated voltage of the electric motor. Hereinafter, the driving current and the driving voltage will be collectively referred to as sampled parameters.

To define a corresponding relationship between values of the sampled parameter and consumed lifespans, a value of the sampled parameter is measured when the purifier is operated with a new filter core, and this value is taken as a first sampled parameter. Then, a value of the sampled parameter is measured when the purifier is operated with the filter core reaching an end of its rated service life, and this value is taken as a second sampled parameter. Here, the technology for measuring the sampled parameter of the electric motor will not be repeated in this embodiment.

In step 203, a range between the first sampled parameter and the second sampled parameter is determined.

For example, when the sampled parameter is the current, it is assumed that the first sampled parameter is 3 A, and the second sampled parameter is 2 A, then the range is determined as [2, 3].

In step 204, a corresponding relationship between the values in the range and consumed lifespans is defined.

In this embodiment, a calculation formula of the values and the consumed lifespans can be generated, or a corresponding relationship between values and consumed lifespans can be formed, or by other means, which will not be limited in this embodiment.

Figure 2B:
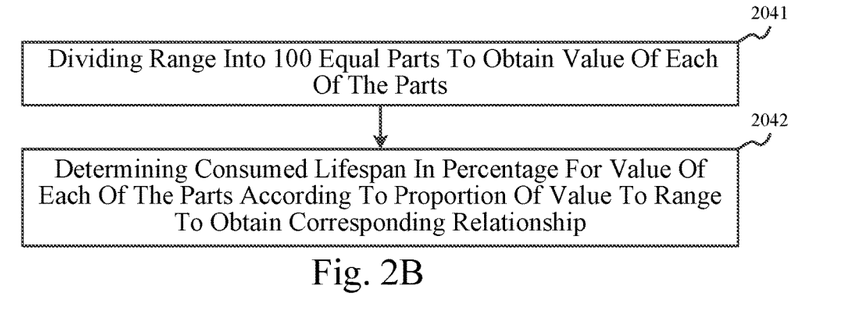
FIG. 2B is a flow chart illustrating a process for defining a corresponding relationship according to the exemplary embodiment.

FIG. 2B is a flow chart illustrating a process for defining a corresponding relationship. When the consumed lifespans are indicated in percentages, the step of defining a corresponding relationship between the values in the range and consumed lifespans includes the following steps.

In step 2041, the range is divided into 100 equal parts to obtain a value of each of the parts.

In step 2042, a consumed lifespan in percentage for the value of each of the parts is determined according to a proportion of the value to the range to obtain the corresponding relationship.

For example, when the range is [2, 3], by dividing the range into 100 equal parts, a value of each of the parts can be obtained, respectively 2, 2.01, 2.02, . . . , 2.98, 2.99 and 3. A consumed lifespan in percentage 0% is determined as corresponding to the value 2, 1% corresponding to 2.01, 2% corresponding to 2.02, . . . , 98% corresponding to 2.98, 99% corresponding to 2.99 and 100% corresponding to 3.

By dividing the range into 100 equal parts to obtain a value of each of the parts, and defining a corresponding relationship between the values of the parts and percentages, the consumed lifespans can be finely measured. Thus, the accuracy of calculating consumed lifespans is improved.

Here, the process of steps 201-204 can be performed to define a corresponding relationship between the values of the sampled parameter and the consumed lifespans. They can be performed prior to the step 207, but the order of the steps 201-204 and the steps 205, 206 is not limited.

In step 205, an electric motor of a purifier is controlled to rotate at a predetermined speed.

The predetermined speed in this step is the same as the speed manually adjusted by the user in step 201.

By keeping the speed when calculating the consumed lifespans the same as the speed when defining the corresponding relationship, it can eliminate the effect of the speed on the sampled parameter of the electric motor. Then, the dirty degree of the filter core is only positive correlated to the value of the driving current of the electric motor. In this way, it can improve the accuracy of calculating consumed lifespans.

In step 206, a value of a sampled parameter of the electric motor is acquired, the sampled parameter being at least one of a sampled current and a sampled voltage of the electric motor.

Figure 2C:
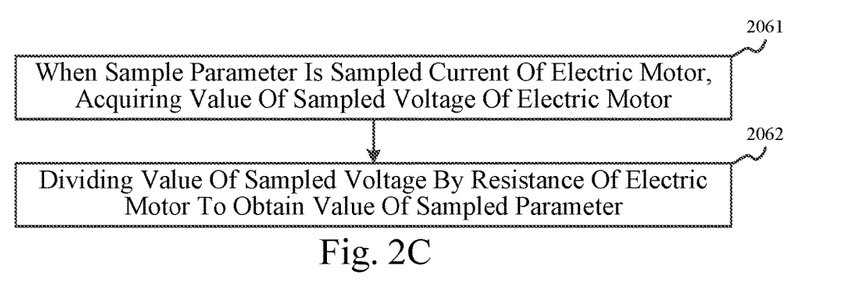
FIG. 2C is a flow chart illustrating a process for acquiring a value of a sampled parameter according to the exemplary embodiment.

When the sample parameter is a sampled voltage of the electric motor, the value of the sampled voltage can be directly acquired by a method known in the related art. When the sample parameter is a sampled current of the electric motor, FIG. 2C shows a flow chart illustrating a process for acquiring a value of a sampled parameter. Here, the step of acquiring a value of a sampled parameter of the electric motor includes the following steps.

In step 2061, when the sample parameter is a sampled current of the electric motor, a value of the sampled voltage of the electric motor is acquired.

In step 2062, the value of the sampled voltage is divided by a resistance of the electric motor to obtain the value of the sampled parameter.

Since the value of the resistance of the electric motor has been known, and the value of the sample voltage can be directly acquired by a method known in the related art, then the value of the sampled voltage can be divided by the resistance to obtain the value of the sampled current, i.e. the sampled parameter.

In step 207, a pre-defined corresponding relationship is retrieved. The pre-defined corresponding relationship is used for storing relations between values of the sampled parameter and consumed lifespans.

In step 208, a consumed lifespan corresponding to the acquired value of the sampled parameter is searched for in the corresponding relationship, wherein the consumed lifespan is in positive correlation with the acquired value of the sampled parameter.

For example, it is assumed that the value of the sample parameter is 2.54 A and in the corresponding relationship, the value 2.54 corresponds to a percentage 54%, then, the consumed lifespan of the filter core can be determined as 54%.

In the method for calculating a consumed lifespan provided by the present disclosure, an electric motor of a purifier is controlled to rotate at a predetermined speed; a value of a sampled parameter of the electric motor is acquired, the sampled parameter being at least one of a sampled current and a sampled voltage of the electric motor; and a consumed lifespan of the purifier is determined according to the acquired value of the sampled parameter, wherein the consumed lifespan is in positive correlation with the acquired value of the sampled parameter. Thus, based on the fact that the dirty degree of the filter core is in positive correlation with the value of the driving current of the electric motor, the dirty degree of the filter core can be determined according to the value of the sampled parameter of the electric motor, and in turn, the consumed lifespan of the filter core can be determined. In this way, it can avoid inaccuracies of determining the consumed lifespans according to the service time periods, and can improve the accuracy of calculating consumed lifespans.

In addition, by keeping the speed when calculating the consumed lifespans the same as the speed when defining the corresponding relationship, it can eliminate the effect of the speed on the sampled parameter of the electric motor. Then, the dirty degree of the filter core is only positive correlated to the value of the driving current of the electric motor. In this way, the accuracy of calculating consumed lifespans is improved.

Further, by dividing the range into 100 equal parts to obtain a value of each of the parts, and determining a consumed lifespan in percentage for the value of each of the parts according to a proportion of the value to the range to obtain the corresponding relationship, a corresponding relationship may be defined between the values of each of the 100 equal parts and consumed lifespans in percentages, the consumed lifespans can be finely measured. Thus, the accuracy of calculating consumed lifespans is improved.

Figure 3:
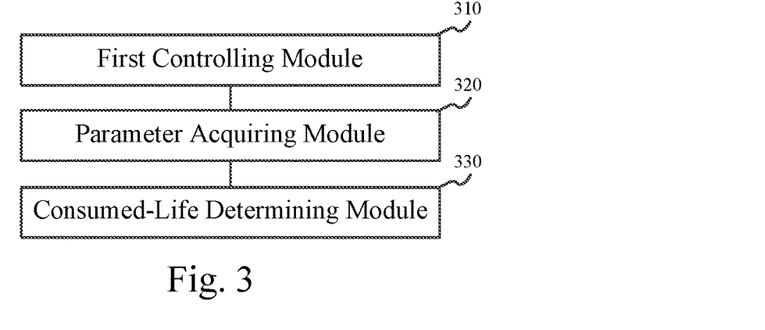
FIG. 3 is a block diagram illustrating a device for calculating a consumed lifespan according to an exemplary embodiment.

FIG. 3 is a block diagram illustrating a device for calculating a consumed lifespan according to an exemplary embodiment. The device for calculating a consumed lifespan is applied in a purifier. As shown in FIG. 3, the device for calculating a consumed lifespan includes a first controlling module 310, a parameter acquiring module 320 and a consumed-life determining module 330.

The first controlling module 310 is configured to control an electric motor of a purifier to rotate at a predetermined speed. The parameter acquiring module 320 is configured to acquire a value of a sampled parameter of the electric motor, the sampled parameter being at least one of a sampled current and a sampled voltage of the electric motor. The consumed-life determining module 330 is configured to determine a consumed lifespan of the purifier according to the value of the sampled parameter obtained by the parameter acquiring module 320, wherein the consumed lifespan is in positive correlation with the acquired value of the sampled parameter.

In the device for calculating a consumed lifespan provided by the present disclosure, an electric motor of a purifier is controlled to rotate at a predetermined speed; a value of a sampled parameter of the electric motor is acquired, the sampled parameter being at least one of a sampled current and a sampled voltage of the electric motor; and a consumed lifespan of the purifier is determined according to the acquired value of the sampled parameter, wherein the consumed lifespan is in positive correlation with the acquired value of the sampled parameter. Thus, based on the fact that the dirty degree of the filter core is in positive correlation with the value of the driving current of the electric motor, the dirty degree of the filter core can be determined according to the value of the sampled parameter of the electric motor, and in turn, the consumed lifespan of the filter core can be determined. In this way, it can avoid the inaccuracies of determining the consumed lifespans according to the service time periods, and can improve the accuracy of calculating consumed lifespans.

Figure 4:
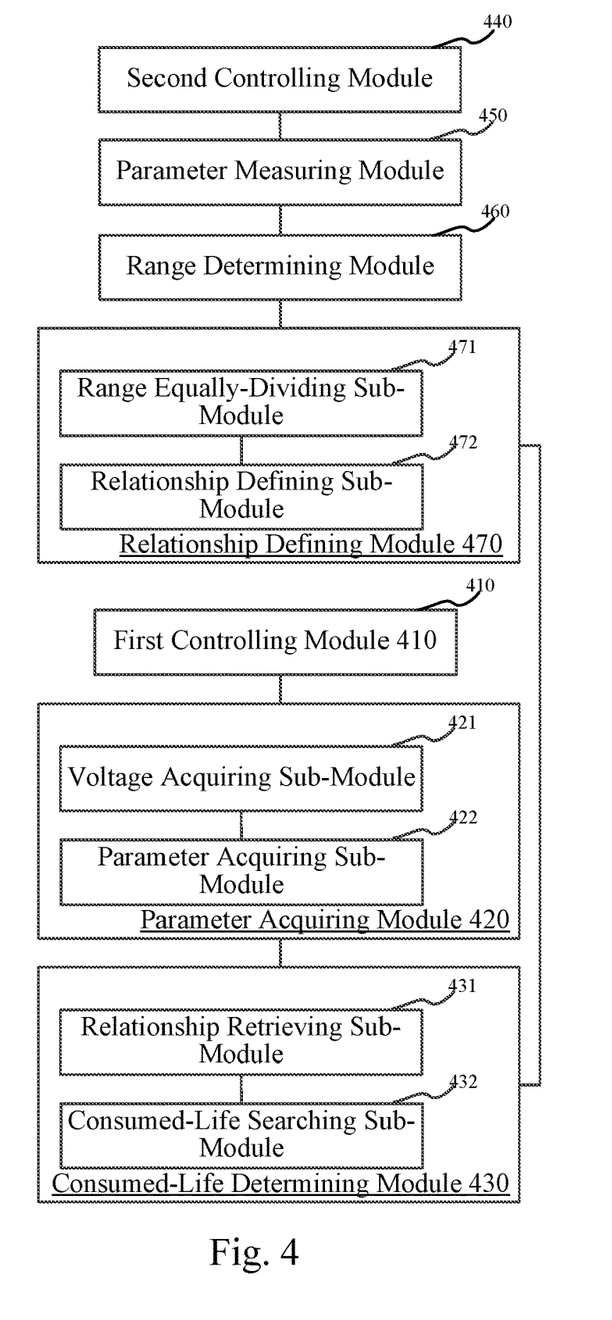
FIG. 4 is a block diagram illustrating a device for calculating a consumed lifespan according to an exemplary embodiment.

FIG. 4 is a block diagram illustrating a device for calculating a consumed lifespan according to an exemplary embodiment. The device for calculating a consumed lifespan is applied in a purifier. As shown in FIG. 4, the device for calculating a consumed lifespan includes a first controlling module 410, a parameter acquiring module 420 and a consumed-life determining module 430.

The first controlling module 410 is configured to control an electric motor of a purifier to rotate at a predetermined speed. The parameter acquiring module 420 is configured to acquire a value of a sampled parameter of the electric motor, the sampled parameter being at least one of a sampled current and a sampled voltage of the electric motor. The consumed-life determining module 430 is configured to determine a consumed lifespan of the purifier according to the value of the sampled parameter obtained by the parameter acquiring module 420, wherein the consumed lifespan is in positive correlation with the acquired value of the sampled parameter.

Optionally, the consumed-life determining module 430 includes: a relationship retrieving sub-module 431 and a consumed-life searching sub-module 432.

The relationship retrieving sub-module 431 is configured to retrieve a pre-defined corresponding relationship. The pre-defined corresponding relationship is used for storing relations between values of the sampled parameter and consumed lifespans. The consumed-life searching sub-module 432 is configured to search for a consumed lifespan corresponding to the acquired value of the sampled parameter in the corresponding relationship obtained by the relationship retrieving sub-module 431.

Optionally, the device for calculating a consumed lifespan further includes: a second controlling module 440, a parameter measuring module 450, a range determining module 460 and a relationship defining module 470.

The second controlling module 440 is configured to control the electric motor of the purifier to rotate at the predetermined speed. The parameter measuring module 450 is configured to measure a first sampled parameter of the electric motor and a second sampled parameter of the electric motor, the first sampled parameter being a value of the sampled parameter when the purifier is operated with a new filter core, and the second sampled parameter being a value of the sampled parameter when the purifier is operated with the filter core reaching an end of its rated service life. The range determining module 460 is configured to determine a range between the first sampled parameter and the second sampled parameter obtained by the parameter measuring module 450. The relationship defining module 470 is configured to define a corresponding relationship between the values in the range determined by the range determining module 460 and consumed lifespans.

Optionally, when the consumed lifespans are indicated in percentages, the relationship defining module 470 includes: a range equally-dividing sub-module 471 and a relationship defining sub-module 472.

The range equally-dividing sub-module 471 is configured to divide the range into 100 equal parts, to obtain a value of each of the parts. The relationship defining sub-module 472 is configured to determine a consumed lifespan in percentage for the value of each of the parts obtained by the range equally-dividing sub-module 471 according to a proportion of the value to the range, to obtain the corresponding relationship.

Optionally, the parameter acquiring module 420 includes: a voltage acquiring sub-module 421 and a parameter acquiring sub-module 422.

The voltage acquiring sub-module 421 is configured to, when the sample parameter is a sampled current of the electric motor, acquire a value of the sampled voltage of the electric motor. The parameter acquiring sub-module 422 is configured to divide the value of the sampled voltage obtained by the voltage acquiring sub-module 421 by a resistance of the electric motor to obtain the value of the sampled parameter.

In the device for calculating a consumed lifespan provided by the present disclosure, an electric motor of a purifier is controlled to rotate at a predetermined speed; a value of a sampled parameter of the electric motor is acquired, the sampled parameter being at least one of a sampled current and a sampled voltage of the electric motor; and a consumed lifespan of the purifier is determined according to the acquired value of the sampled parameter, wherein the consumed lifespan is in positive correlation with the acquired value of the sampled parameter. Thus, based on the fact that the dirty degree of the filter core is in positive correlation with the value of the driving current of the electric motor, the dirty degree of the filter core can be determined according to the value of the sampled parameter of the electric motor, and in turn, the consumed lifespan of the filter core can be determined. In this way, it can avoid the inaccuracies of determining the consumed lifespans according to the service time periods, and can improve the accuracy of calculating consumed lifespans.

In addition, by keeping the speed when calculating the consumed lifespans the same as the speed when defining the corresponding relationship, it can eliminate the effect of the speed on the sampled parameter of the electric motor. Then, the dirty degree of the filter core is only positive correlated to the value of the driving current of the electric motor. In this way, it can improve the accuracy of calculating consumed lifespans.

Further, by dividing the range into 100 equal parts to obtain a value of each of the parts, and determining a consumed lifespan in percentage for the value of each of the parts according to a proportion of the value to the range to obtain the corresponding relationship, a corresponding relationship may be defined between the values of each of the 100 equal parts and consumed lifespans in percentages, the consumed lifespans can be finely measured, the accuracy of calculating consumed lifespans can be improved.

With respect to the devices in the above embodiments, the specific manners for performing operations for individual modules therein have been described in detail in the embodiments regarding the relevant methods, which will not be elaborated herein.

An exemplary embodiment of the present disclosure provides a device for calculating a consumed lifespan, which can implement the method for calculating a consumed lifespan provided by the present disclosure. The device for calculating a consumed lifespan includes: a processor and a memory for storing instructions executable by the processor. Wherein the processor is configured to perform: controlling an electric motor of a purifier to rotate at a predetermined speed; acquiring a value of a sampled parameter of the electric motor, the sampled parameter being at least one of a sampled current and a sampled voltage of the electric motor; and determining a consumed lifespan of the purifier according to the acquired value of the sampled parameter, wherein the consumed lifespan is in positive correlation with the acquired value of the sampled parameter.

Figure 5:
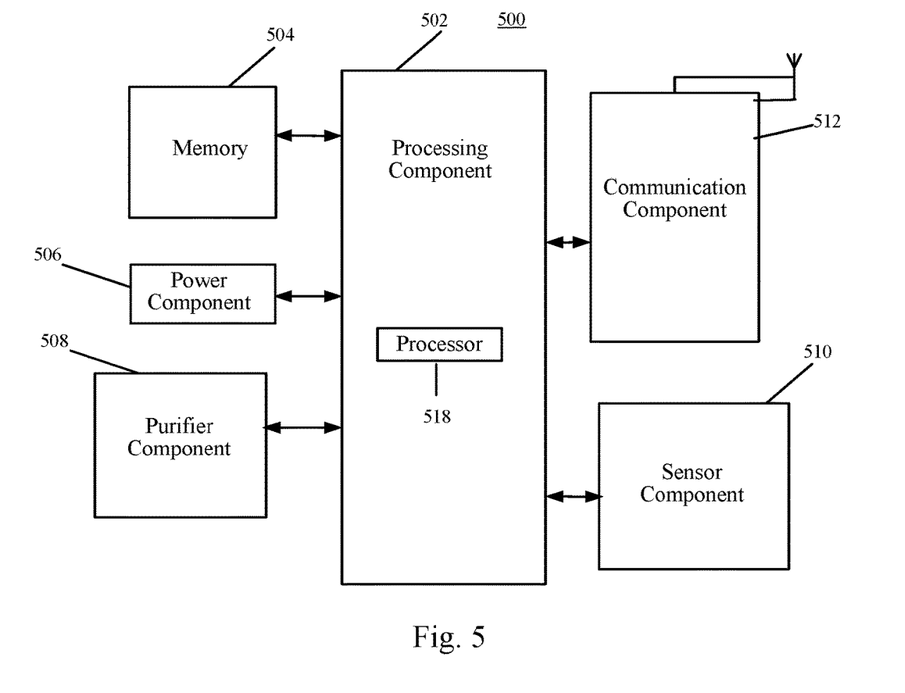
FIG. 5 is a block diagram illustrating a device for calculating a consumed lifespan according to an exemplary embodiment.

FIG. 5 is a block diagram of a device 500 for purifying the air according to an exemplary embodiment. For example, the device 500 may be a purifier.

Referring to FIG. 5, the device 500 may include one or more of the following components: a processing component 502, a memory 504, a power component 506, a purifier component 508, a sensor component 510, and a communication component 512.

The processing component 502 typically controls overall operations of the device 500. The processing component 502 may include one or more processors 518 to execute instructions to perform all or part of the steps in the methods described in the above embodiments. Moreover, the processing component 502 may include one or more modules which facilitate the interaction between the processing component 502 and other components. For instance, the processing component 502 may interact with the sensor component 510 and the communication component 512, and so on.

The memory 504 is configured to store various types of data to support the operation of the device 500. Examples of such data include instructions for any applications or methods operated on the device 500, etc. The memory 504 may be implemented using any type of volatile or non-volatile memory devices, or a combination thereof, such as a static random access memory (SRAM), an electrically erasable programmable read-only memory (EEPROM), an erasable programmable read-only memory (EPROM), a programmable read-only memory (PROM), a read-only memory (ROM), a magnetic memory, a flash memory, a magnetic or optical disk.

The power component 506 provides power to various components of the device 500. The power component 506 may include a power management system, one or more power sources, and any other components associated with the generation, management, and distribution of power in the device 500.

The purifier component 508 includes an electric motor and is configured to purify the air sucked in and discharge the purified air. In one implementation, the purifier component 508 purifies the air by absorbing harmful substances in the air. In another implementation, the purifier component 508 purifies the air by releasing negative oxygen ions. However, the purifier component 508 can also purifies the air by other means, which will be elaborated herein.

The sensor component 510 includes one or more sensors to provide status assessments of various aspects of the device 500. For instance, the sensor component 510 may detect concentration of dust in the air.

The communication component 512 is configured to facilitate communication, wired or wirelessly, between the device 500 and other devices. The device 500 can access a wireless network based on a communication standard, such as WiFi, 2G, or 3G, or a combination thereof. In one exemplary embodiment, the communication component 512 receives a broadcast signal or broadcast associated information from an external broadcast management system via a broadcast channel. In one exemplary embodiment, the communication component 512 further includes a near field communication (NFC) module to facilitate short-range communications. For example, the NFC module may be implemented based on a radio frequency identification (RFID) technology, an infrared data association (IrDA) technology, an ultra-wideband (UWB) technology, a Bluetooth (BT) technology, and other technologies.

In exemplary embodiments, the device 500 may be implemented with one or more application specific integrated circuits (ASICs), digital signal processors (DSPs), digital signal processing devices (DSPDs), programmable logic devices (PLDs), field programmable gate arrays (FPGAs), controllers, micro-controllers, microprocessors, or other electronic components, for performing the above described methods.

In exemplary embodiments, there is also provided a non-transitory computer-readable storage medium including instructions, such as included in the memory 504, executable by the processor 518 in the device 500, for performing the above-described methods. For example, the non-transitory computer-readable storage medium may be a ROM, a RAM, a CD-ROM, a magnetic tape, a floppy disc, an optical data storage device, and the like.

Other embodiments will be apparent to those skilled in the art from consideration of the specification and practice of the embodiments disclosed here. This application is intended to cover any variations, uses, or adaptations of the embodiments following the general principles thereof and including such departures from the present disclosure as come within known or customary practice in the art. It is intended that the specification and embodiments be considered as exemplary only, with a true scope and spirit of the invention being indicated by the following claims.

It will be appreciated that the present invention is not limited to the exact construction that has been described above and illustrated in the accompanying drawings, and that various modifications and changes can be made without departing from the scope thereof. It is intended that the scope of the invention only be limited by the appended claims.

What is claimed is:

1. A method for calculating a consumed lifespan, comprising followings steps:

controlling an electric motor of a purifier to rotate at a predetermined speed;

acquiring a value of a sampled parameter of the electric motor rotating at the predetermined speed, the sampled parameter being at least one of a sampled current and a sampled voltage of the electric motor; and determining a consumed lifespan of the purifier according to the acquired value of the sampled parameter and a pre-defined corresponding relationship, wherein the pre-defined corresponding relationship is used for storing relations between values of the sampled parameter and consumed lifespans, the relations between values of the sampled parameter and consumed lifespans are obtained under a condition that the electric motor of the purifier rotates at the predetermined speed, and the determined consumed lifespan is in positive correlation with the acquired value of the sampled parameter.

2. The method of claim 1, wherein the step of determining a consumed lifespan of the purifier according to the acquired value of the sampled parameter comprises:

retrieving the pre-defined corresponding relationship; and searching for a consumed lifespan corresponding to the acquired value of the sampled parameter in the pre-defined corresponding relationship.

3. The method of claim 2, wherein the method further comprises following steps:

controlling the electric motor of the purifier to rotate at the predetermined speed;

measuring a first sampled parameter of the electric motor and a second sampled parameter of the electric motor rotating at the predetermined speed, the first sampled parameter being a value of the sampled parameter when the purifier is operated with a new filter core, and the second sampled parameter being a value of the sampled parameter when the purifier is operated with the filter core reaching an end of its rated service life;

determining a range between the first sampled parameter and the second sampled parameter; and defining a corresponding relationship between the values in the range and consumed lifespans as the pre-defined corresponding relationship.

4. The method of claim 3, wherein when the consumed lifespans are indicated in percentages, the step of defining a corresponding relationship between the values in the range and consumed lifespans comprises:

dividing the range into 100 equal parts to obtain a value of each of the parts; and determining a consumed lifespan in percentage for the value of each of the parts according to a proportion of the value to the range to obtain the corresponding relationship.

5. The method of claim 1, wherein the step of acquiring a value of a sampled parameter of the electric motor comprises:

when the sample parameter is a sampled current of the electric motor, acquiring a value of the sampled voltage of the electric motor; and dividing the value of the sampled voltage by a resistance of the electric motor to obtain the value of the sampled parameter.

6. The method of claim 2, wherein the step of acquiring a value of a sampled parameter of the electric motor comprises:

when the sample parameter is a sampled current of the electric motor, acquiring a value of the sampled voltage of the electric motor; and dividing the value of the sampled voltage by a resistance of the electric motor to obtain the value of the sampled parameter.

7. The method of claim 3, wherein the step of acquiring a value of a sampled parameter of the electric motor comprises:
when the sample parameter is a sampled current of the electric motor, acquiring a value of the sampled voltage of the electric motor; and
dividing the value of the sampled voltage by a resistance of the electric motor to obtain the value of the sampled parameter.

8. The method of claim 4, wherein the step of acquiring a value of a sampled parameter of the electric motor comprises:
when the sample parameter is a sampled current of the electric motor, acquiring a value of the sampled voltage of the electric motor; and
dividing the value of the sampled voltage by a resistance of the electric motor to obtain the value of the sampled parameter.

9. A device for calculating a consumed lifespan, comprising:
a processor; and
a memory for storing instructions executable by the processor;
wherein the processor is configured to perform:
controlling an electric motor of a purifier to rotate at a predetermined speed;
acquiring a value of a sampled parameter of the electric motor rotating at the predetermined speed, the sampled parameter being at least one of a sampled current and a sampled voltage of the electric motor; and
determining a consumed lifespan of the purifier according to the acquired value of the sampled parameter and a pre-defined corresponding relationship, wherein the pre-defined corresponding relationship is used for storing relations between values of the sampled parameter and consumed lifespans, the relations between values of the sampled parameter and consumed lifespans are obtained under a condition that the electric motor of the purifier rotates at the predetermined speed, and the determined consumed lifespan is in positive correlation with the acquired value of the sampled parameter.

10. The device of claim 9, wherein determining a consumed lifespan of the purifier according to the acquired value of the sampled parameter comprises:
retrieving the pre-defined corresponding relationship; and
searching for a consumed lifespan corresponding to the acquired value of the sampled parameter in the pre-defined corresponding relationship.

11. The device of claim 10, wherein the processor is further configured to perform:
controlling the electric motor of the purifier to rotate at the predetermined speed;
measuring a first sampled parameter of the electric motor and a second sampled parameter of the electric motor rotating at the predetermined speed, the first sampled parameter being a value of the sampled parameter when the purifier is operated with a new filter core, and the second sampled parameter being a value of the sampled parameter when the purifier is operated with the filter core reaching an end of its rated service life;
determining a range between the first sampled parameter and the second sampled parameter; and
defining a corresponding relationship between the values in the range and consumed lifespans as the pre-defined corresponding relationship.

12. The device of claim 11, wherein when the consumed lifespans are indicated in percentages, defining a corresponding relationship between the values in the range and consumed lifespans comprises:
dividing the range into 100 equal parts to obtain a value of each of the parts; and
determining a consumed lifespan in percentage for the value of each of the parts according to a proportion of the value to the range to obtain the corresponding relationship.

13. The device of claim 9, wherein acquiring a value of a sampled parameter of the electric motor comprises:
when the sample parameter is a sampled current of the electric motor, acquiring a value of the sampled voltage of the electric motor; and
dividing the value of the sampled voltage by a resistance of the electric motor to obtain the value of the sampled parameter.

14. The device of claim 10, wherein acquiring a value of a sampled parameter of the electric motor comprises:
when the sample parameter is a sampled current of the electric motor, acquiring a value of the sampled voltage of the electric motor; and
dividing the value of the sampled voltage by a resistance of the electric motor to obtain the value of the sampled parameter.

15. The device of claim 11, wherein acquiring a value of a sampled parameter of the electric motor comprises:
when the sample parameter is a sampled current of the electric motor, acquiring a value of the sampled voltage of the electric motor; and
dividing the value of the sampled voltage by a resistance of the electric motor to obtain the value of the sampled parameter.

16. A non-transitory computer-readable storage medium having stored therein instructions that, when executed by a processor of a purifier, causes the purifier to perform a method for calculating a consumed lifespan, the method comprising the following steps:
controlling an electric motor of a purifier to rotate at a predetermined speed;
acquiring a value of a sampled parameter of the electric motor rotating at the predetermined speed, the sampled parameter being at least one of a sampled current and a sampled voltage of the electric motor; and
determining a consumed lifespan of the purifier according to the acquired value of the sampled parameter and a pre-defined corresponding relationship, wherein the pre-defined corresponding relationship is used for storing relations between values of the sampled parameter and consumed lifespans, the relations between values of the sampled parameter and consumed lifespans are obtained under a condition that the electric motor of the purifier rotates at the predetermined speed, and the determined consumed lifespan is in positive correlation with the acquired value of the sampled parameter.

* * * * *